US00PP23612P3

(12) United States Plant Patent
Yencho et al.

(10) Patent No.: US PP23,612 P3
(45) Date of Patent: May 21, 2013

(54) SWEETPOTATO PLANT NAMED 'NCORNSP-013GNLC'

(50) Latin Name: ***Ipomoea batatas* (L.) Lam.**
Varietal Denomination: NCORNSP-013GNLC

(75) Inventors: G. Craig Yencho, Raleigh, NC (US); Kenneth V. Pecota, Raleigh, NC (US); Meri K. Reeber, Apex, NC (US)

(73) Assignee: North Carolina State University, Raleigh, NC (US)

( * ) Notice: Subject to any disclaimer, the term of this patent is extended or adjusted under 35 U.S.C. 154(b) by 35 days.

(21) Appl. No.: 13/065,468

(22) Filed: Mar. 22, 2011

(65) Prior Publication Data

US 2012/0246772 P1 Sep. 27, 2012

(51) Int. Cl.
*A01H 5/00* (2006.01)

(52) U.S. Cl.
USPC ..... Plt./258

(58) Field of Classification Search ..... Plt./258
See application file for complete search history.

(56) References Cited

PUBLICATIONS

Office Action from the United States Patent and Trademark Office for U.S. Appl. No. 13/065,463 dated Sep. 11, 2012 (10 pages).
Office Action from the United States Patent and Trademark Office for U.S. Appl. No. 13/065,464 dated Sep. 10, 2012 (9 pages).
United States Patent Office Notice of Allowance for U.S. Appl. No. 13/065,463 dated Jan. 14, 2013 (6 pages).
United States Patent Office Notice of Allowance for U.S. Appl. No. 13/065,464 dated Jan. 14, 2013 (6 pages).

*Primary Examiner* — June Hwu
(74) *Attorney, Agent, or Firm* — Michael Best & Friedrich LLP

(57) ABSTRACT

'NCORNSP-013GNLC' is new and distinct variety of ornamental sweetpotato. It is a compact, semi-upright; mounding, spreading, cultivar producing many short shoots. This ornamental sweetpotato variety is distinguishable from other cultivars by its burgundy red leaves that have 5-7 extremely deep lobes; a compact habit and semi-erect mounding plant architecture. Furthermore, 'NCORNSP-013GNLC' has a very good vigor, is very well branched and is desirable for production as a landscape or containerized plant. The production of flowers by 'NCORNSP-013GNLC' is moderate under short day conditions.

3 Drawing Sheets

Latin name of the genus and species: *Ipomoea batatas* (L.) Lam.

Variety denomination: 'NCORNSP-013GNLC'.

BACKGROUND

*Ipomoea batatas* is a member of the morning glory family Convolvulaceae. This species is grown worldwide and exhibits a range of plant forms and colors. The cultivated members of *Ipomoea batatas* grown by farmers are commonly produced for consumption of their enlarged storage roots. Such plants typically produce a fast growing green vine that has a wide variety of leaf shapes ranging from palmate and deeply lobed, to cordate or triangular shaped leaves with no lobes.

Ornamental sweetpotato plants, like their edible forms, are typically a heat-loving, drought-tolerant, perennial vine typically, grown as an annual. However, ornamental sweetpotato plants are distinguished from the edible cultivated forms in that they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g. pale yellow to dark purple with some exhibiting temporal and individual leaf color variegation patterns) and plant shapes (e.g. mounded and very compact to prostrate and highly spreading). They can be grown in a potted plant and/or mixed planting format, and they have the ability to cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

Applicants desire to produce new cultivars of ornamental sweetpotato with new or improved foliage colors, variegation patterns, leaf shapes, and plant architectures. In addition, applicants believe it would be advantageous to develop cultivars of ornamental sweetpotato exhibiting a more compact growth that do not out-compete other species in mixed containers.

'NCORNSP-013GNLC' addresses at least one of the above mentioned needs.

Lineage. 'NCORNSP-013GNLC' (breeding designation NC6176-002ORN) originated from a conventional cross between the proprietary *Ipomoea batatas* breeding lines NC4263-006ORN (the female parent; not patented) and NC4691-004ORN (the male parent; not patented). Botanical seed was harvested from this and other ornamental sweetpotato clones planted in our winter greenhouse crossing block between September of 2007 and April of 2008 in Raleigh, N.C. NC4263-006ORN resulted from a conventional cross between the proprietary *Ipomoea batatas* breeding lines NC1928-001ORN (the female parent; not patented) and NC0953-036ORN (the male parent; not patented). NC4691-004ORN resulted from a cross between the proprietary *Ipomoea batatas* breeding lines NC2349-001ORN (the female parent; not patented) and NC3000-001ORN (the male parent;

not patented). Botanical seed from this family were planted in the greenhouse in Spring 2008. The first cycle of selection on the population was exercised in the seedling trays and survivors were transferred to a single 6-inch pot, which was then maintained in the greenhouse. Cuttings (2 each) were taken from the plants in May and planted in the field as 2-plant unreplicated plots during early July 2008. The single, individual plant now known as 'NCORNSP-013GNLC' was selected Aug. 15, 2008 because of its combination of exceptional features, and has been propagated asexually in Raleigh, N.C. since that time.

Asexual Reproduction. Since its selection, 'NCORNSP-013GNLC' has been asexually reproduced in Raleigh, N.C. predominantly by vegetative propagation of vine cuttings. Successively, there have been three cycles of vegetative propagation, one cycle of tissue culture micropropagation, and multiple vegetative propagation cycles to increase the plant population. Asexual reproduction of 'NCORNSP-013GNLC' by cuttings has shown that the unique features of the new cultivar are stable and the plant reproduces true-to-type in successive generations.

REFERENCE TO PLANT BREEDERS RIGHTS

Plant Breeders Rights for 'NCORNSP-013GNLC' have not been applied for. 'NCORNSP-013GNLC' has not been made publicly available or sold more than one year prior to the date of this application.

SUMMARY

'NCORNSP-013GNLC' is a compact, semi-upright; mounding, spreading variety producing many short shoots. It is distinguishable from other cultivars by its burgundy red leaves that have 5-7 extremely deep lobes; a compact habit and semi-erect mounding plant architecture. The extremely deep lobed feature of the leaves of this plant and the plant architecture makes 'NCORNSP-013GNLC' unique amongst the current ornamental sweetpotatoes in the marketplace. 'NCORNSP-013GNLC' exhibits very good vigor and is very well branched. In greenhouse and field trials conducted since 2008 by the breeding program and industry collaborators 'NCORNSP-013GNLC' has been shown to be much less vigorous than *Ipomoea batatas* 'Margarita' and 'Blackie' and is suitable for use as a landscape or containerized plant. The production of flowers by 'NCORNSP-013GNLC' is moderate under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED DESCRIPTION OF THE NEW VARIETY

The following is a detailed description of the botanical characteristics of a new and distinct cultivar of *Ipomoea batatas* plant known by the cultivar name 'NCORNSP-013GNLC'. All colors cited herein refer to *The Royal Horticultural Society Colour Chart* designations (The Royal Horticultural Society, London, 2007, $5^{th}$ ed.) except where general terms of ordinary dictionary significance are used. Plant descriptions are based on standardized international sweetpotato descriptors established jointly by the International Potato Center (CIP), Lima, Peru; The Asian Vegetable Research and Development Center (AVRDC), Taipei, Taiwan; and the International Board for Plant Genetic Resources (IBPGR), Rome, Italy (CIP, AVRDC, IBPGR. 1991. Descriptors for Sweet Potato. Huaman, Z., editor. International Board for Plant Genetic Resources, Rome, Italy, 134 pp.). Where dimensions, sizes, colors, and other characteristics are given, it is to be understood that such characteristics are approximations or averages set forth as accurately as practicable.

The descriptions reported herein are from 62-day-old specimens grown individually in six-inch azalea pots. The plants were grown in Raleigh, N.C., under commercial practice in a glass-covered greenhouse, where, during the fall, day and night temperatures range between 18-30 C and 15-21 C, respectively. Plant ratings were taken during the last week in November 2010. 'NCORNSP-013GNLC' has not been observed under all possible environmental conditions; therefore, the phenotype may vary with variations in the environment such as season, temperature, light intensity, day length, cultural conditions, and the like.

Classification:

*Botanical name.*—*Ipomoea batatas* (L.) Lam.

*Common name.*—Ornamental Sweetpotato.

*Variety name.*—'NCORNSP-013GNLC'.

Growth conditions: 'NCORNSP-013GNLC' has excellent vigor, a moderate to rapid growth rate, and is very adaptable to container culture. In locales with mild winter conditions, *Ipomoea batatas* 'NCORNSP-013GNLC' will grow perennially; otherwise it is an annual plant. Similar to cultivated sweetpotatoes, wind or rain rarely causes much damage to 'NCORNSP-013GNLC', but if damage does occur, the plant drops the damaged leaves and grows new shoots at nodes where the leaves were lost. Under low light levels in a greenhouse, 'NCORNSP-013GNLC' can develop intumescence, which will remain on the affected foliage, but will be outgrown with new foliage.

Figure 1:
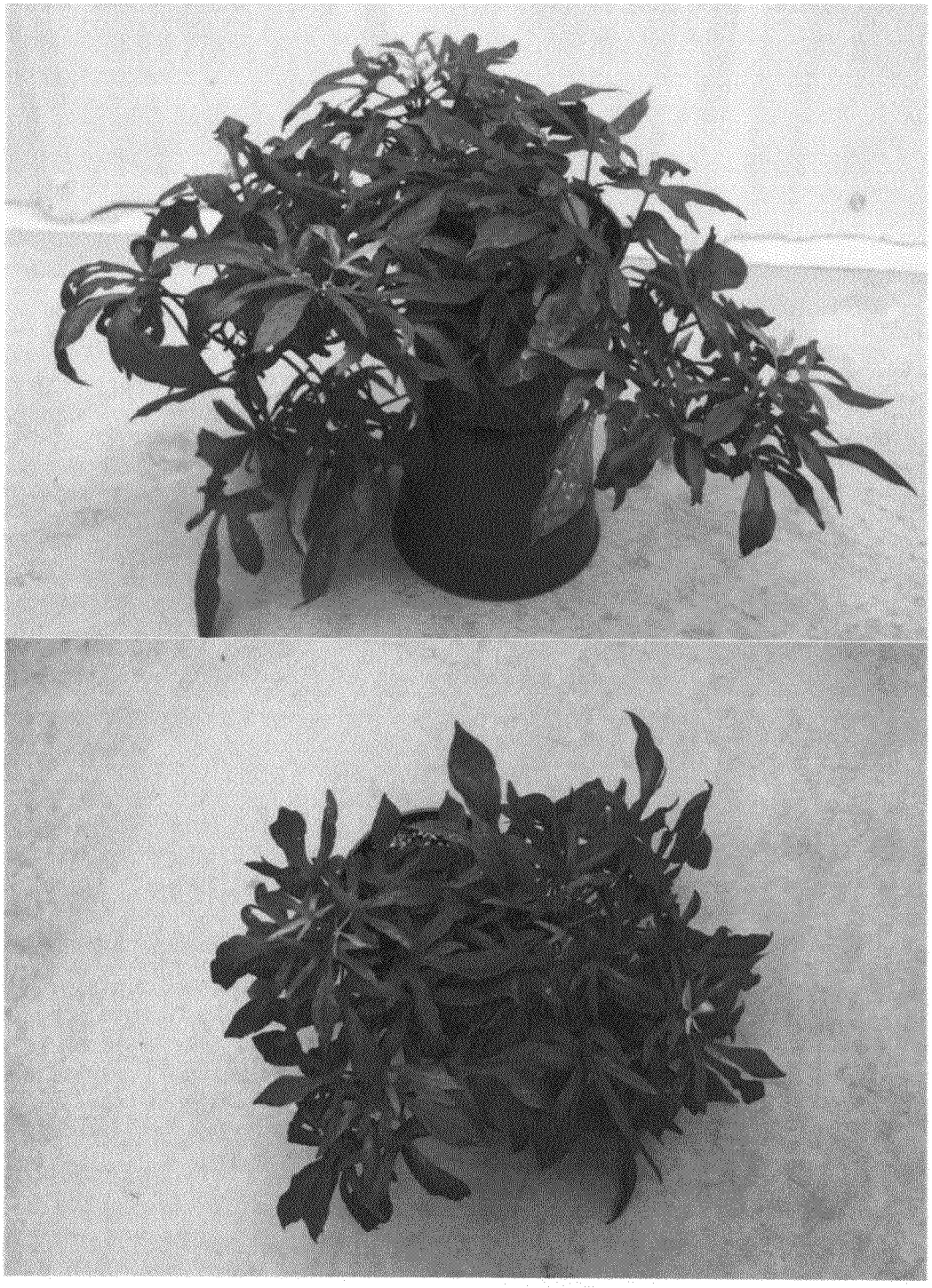
FIG. 1 is a color photograph of a typical specimen of greenhouse grown *Ipomoea batatas* 'NCORNSP-013GNLC' in a 6-inch pot from the side and top, 84 days after planting.
Figure 2:
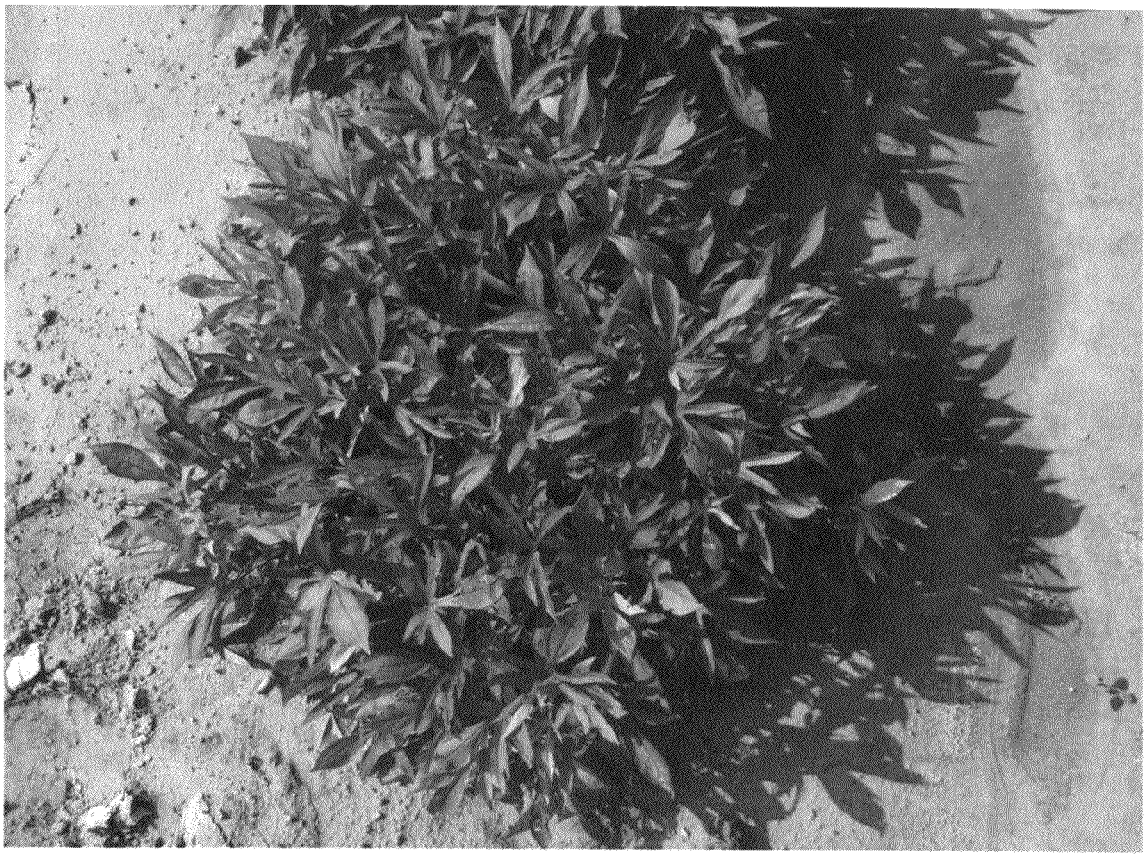
FIG. 2 is a color photograph of a typical specimen of *Ipomoea batatas* 'NCORNSP-013GNLC' from the top in the field, 53 days after planting.
Figure 3:
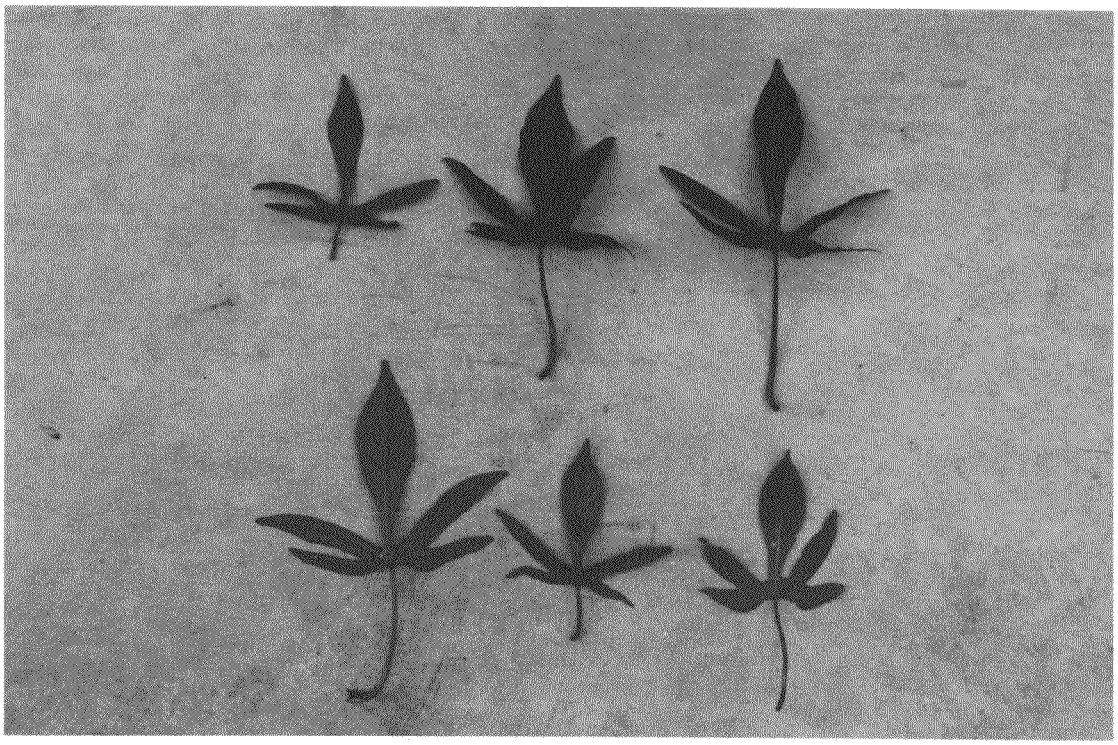
FIG. 3 is a color photograph showing the variety of leaves produced by *Ipomoea batatas* 'NCORNSP-013GNLC' 84 days after planting.

Aboveground structure and coloration: FIGS. 1 and 2 show the shape and coloration of a typical specimen of *Ipomoea batatas* 'NCORNSP-013GNLC'. Color will vary somewhat due to temperature and nutrient stress, which affect the anthocyanin pigments (which give rise to the burgundy purple color). Overall, this cultivar is a compact, semi-upright, mounded, spreading herbaceous plant that has an average height of 16.4 cm and an average area of spread of 47.7 cm. The growth habit of this plant is to grow upright with shoots growing outward.

Branches:

*Branching habitat.*—Freely-branching with ~5 lateral branches coming off the stem. Very dense foliage and no pinching is required to stimulate branching.

*Vegetative lateral branches.*—Length: ~35.3 cm. Diameter: ~0.5 cm. Internodes are short with an average length of ~1.5 cm. Many lateral branches are formed and each axil has latent shoots.

*Stem.*—Round and glabrous with an outward and upward bending aspect with very strong, slightly flexible, non-brittle strength. Color: Burgundy Purple (RHS 59A).

*Petiole.*—Length: ~7.8 cm. Diameter: ~0.3 cm. Color: Burgundy Purple (RHS 59B-59A). Texture: Glabrous.

Foliage: Leaves are alternate and tend to spiral around the stem. They are simple and deeply divided into 5-7 lobes. Leaf shape is somewhat variable, as is leaf size (see FIG. 2).

*Quantity.*—Heavily foliated, with ~33 leaves per lateral branch.

*Mature leaf length.*—~12 cm.

*Mature leaf width.*—~12.7 cm.

*Leaf margin.*—Entire.

*Central lobe width.*—~3.5 cm.

*Central lobe length.*—~10.2 cm.

*Mid-vein lobe length.*—~6.6 cm.

*Mid-vein lobe width.*—~1.4 cm.

*Central lobe shape.*—Narrowly oblanceolate.

*Two axillary lobes.*—Palmate, one long, linear lobe, one broadly oblanceolate.

*Leaf apex.*—Acuminate.

*Leaf base.*—Cordate.

*Texture.*—Glabrous with a matte finish on both upper and lower surface.

*Venation.*—Palmate at the base with arcuate veins in the center lamina.

*Color.*—Leaves go from bright green to burgundy purple as they mature. See also Table 1.

TABLE 1

| Leaf Structure | Upper Surface | Lower Surface |
|---|---|---|
| Young Leaf | Bright green, N144A | Bright green, 145B |
| Mature Leaf | Bronze red, 177A with a bright green base, N144A | Purple Red, N77B-N77A |
| Vein-mature leaf | N77A | N77B |
| Vein-young leaf | N144A | 145B |

Flowers: Flowers occur under short day conditions, but the precise photoperiod for flower induction is currently unknown. Solitary, regular funnelform flowers arising from leaf axils on secondary lateral branches are formed. Peduncles are burgundy purple (RHS 59A) in color. Peduncle width: ~0.2 cm, peduncle length: ~2.2 cm. Flower buds are elliptic to lanceolate and light lavender at the tip (RHS 70B) fading to lighter lavender (RHS N77C) at the base. Flower bud width: ~0.5 cm, flower bud length: ~1.8 cm. Corolla width: ~3.8 cm, corolla length: ~4.1 cm. Limb color: Light lavender, (RHS 76C). The inner throat color gets darker from base to limb going from purple (RHS 84A) at the base to lavender (RHS 84D) near the limb. The limb is rounded. The two outer sepals are shorter than the inner sepals. Average sepal width: ~0.4 cm, average sepal length: ~1.0 cm. The sepals are elliptic and obovate with an obtuse to caudate apex and light green (RHS 1C) to burgundy purple (RHS 59A) in color. Both the upper and lower surfaces of the sepals have a glabrous texture. A single pistil consists of one style topped by one stigma. Pistil averages ~1.8 cm in length. The stigma and style are both cream (RHS NN155A). The stigma is slightly exerted relative to the stamens. The flower averages five stamens. Each stamen consists of a single filament averaging 1.3 cm in length topped with a single anther averaging 0.3 cm in length. Filament color: cream (RHS 159D) fading to light lavender at the base (RHS 76C). Anther color: cream (RHS 159D). Pollen color: cream (RHS 159D). Fruit has not been observed under normal greenhouse conditions.

Storage root coloration: Plants form no, to very small, underground storage roots that are highly malformed and do not meet USDA Sweetpotato Storage Root Grade Standards. Storage roots that do form typically possess cream-colored skin (N155C) with hints of rose (77B). Flesh color is cream (158A).

Comparison with Other *Ipomoea batatas* Cultivars 'NCORNSP-013GNLC' is very distinct based on leaf color, leaf shape, and plant architecture. Of the common cultivars of ornamental sweetpotato, *Ipomoea batatas* 'NCORNSP-013GNLC' is best compared with the 'Sweet Caroline Red' cultivar of U.S. Pat. No. 17,483 (Table 2). Like 'Sweet Caroline Red' of U.S. Pat. No. 17,483, *Ipomoea batatas* 'NCORNSP-013GNLC' has burgundy purple leaves. However, the leaves of 'NCORNSP-013GNLC' are smaller and more deeply lobed than those of 'Sweet Caroline Red' of U.S. Pat. No. 17,483.

'NCORNSP-013GNLC' has a compact, semi-upright, mounding plant habit compared with the moderately trailing habit of 'Sweet Caroline Red' now U.S. Pat. No. 17,483. Furthermore, 'NCORNSP-013GNLC' is highly branched compared with 'Sweet Caroline Red' of U.S. Pat. No. 17,483 resulting in a much denser foliage appearance. As compared with 'Sweet Caroline Red' of U.S. Pat. No. 17,483, 'NCORNSP-013GNLC' has a more upright, mounding, and fuller appearance, making it more suitable for containerized propagation. Unlike 'Sweet Caroline Red' of U.S. Pat. No. 17,483, which rarely produces flowers, 'NCORNSP-013GNLC' will produce flowers under short day conditions.

TABLE 2

| Characteristic | 'NCORNSP-013GNLC' | Female Parent 'NC4263-006ORN' | Male Parent 'NC4691-004ORN'* | 'Sweet Caroline Red' |
|---|---|---|---|---|
| Plant Habit | Compact, Semi-Upright | Trailing | Moderately Compatct, Semi-Upright | Low, Mounding to Trailing |
| Foliage Color | Burgundy purple (RHS 177A, N144A) | Burgundy purple (RHS 177A, N144A) | Purple | Burgundy purple (RHS 177A, N144A) |
| Leaf Size | Moderate | Moderate | Moderate | Moderate-Large |
| Leaf Shape | Very Deeply Lobed | Moderately Lobed, Hastate | Moderately Lobed | Moderately Lobed |

*Male Parent 'NC4691-004ORN' is a breeding line for which no detailed plant characteristics are available.

*Male Parent 'NC4691-004ORN' is a breeding line for which no detailed plant characteristics are available.

Disease or pest resistance: 'NCORNSP-013GNLC' is susceptible to Sweetpotato Feathery Mottle Virus and damage by Japanese beetles. Its resistance or susceptibility to other known insects and pathogens of sweetpotato is unknown.

We claim:

1. A new and distinct cultivar of *Ipomoea batatas* plant named 'NCORNSP-013GNLC', substantially as illustrated and described herein.

* * * * *